United States Patent
Brown et al.

(12)

(10) Patent No.: US 6,365,731 B1
(45) Date of Patent: Apr. 2, 2002

(54) STRIPPING NUCLEIC ACIDS WITH IODINE AND SODIUM THIOSULFATE

(75) Inventors: David Brown; Matthew Winkler, both of Austin, TX (US)

(73) Assignee: Ambion, Inc., Austin, TX (US)

( * ) Notice: Subject to any disclaimer, the term of this patent is extended or adjusted under 35 U.S.C. 154(b) by 0 days.

(21) Appl. No.: 08/907,195

(22) Filed: Aug. 6, 1997

(51) Int. Cl.⁷ .............................. C07H 21/00; C12Q 1/68
(52) U.S. Cl. ....................... 536/25.42; 536/25.3; 435/6; 435/975
(58) Field of Search .................... 435/6, 975; 536/25.3, 536/25.42

(56) References Cited

U.S. PATENT DOCUMENTS 5,700,922 A * 12/1997 Cook ........................ 536/23.1

FOREIGN PATENT DOCUMENTS

| WO | WO 92/10588 | 6/1992 |
| WO | WO 93/15228 | 8/1993 |
| WO | WO 93/17126 | 9/1993 |
| WO | WO 95/09248 | 4/1995 |
| WO | WO 97/27327 | 7/1997 |

OTHER PUBLICATIONS

Goodchild, Bioconjugate Chem., vol. 1(3), Review: Conjugates of Oligonucleotide . . . , May 1990.*

The Merck Index. Eleventh Edition. Published by Merck & Co., Inc. Rahway, NJ, 1989., p. 1370.*

Möller et al. Biotechniques vol. 17, No. 4, pp. 682–684, 1994.*

Chee et al., "Accessing genetic information with high–density DNA arrays," *Science*, 274:610–614, 1996.

Cosstick, "Synthesis and properties of dithymidine phosphate analogues containing 3'–thiothymidine," *Nucleic Acids Research*, 18(4):829–835, 1990.

International Search Report dated Dec. 29, 1998 (PCT/US98/16183) (AMBI:035P).

Jarrett, "Affinity chromotography with nucleic acid polymers," *Journal of Chromotography, Biomedical Applications*, 618:315–339, 1993.

Morse and Bass, "Detection of inosine in messenger RNA by inosine–specific cleavage," *Biochemistry*, 36(28):8429–8434, 1997.

Scadden and Smith, "A ribonuclease speific for inosine–containing RNA: A potential role in antiviral defense," *EMBO Journal*, 16(8):2140–2149, 1997.

* cited by examiner

*Primary Examiner*—Gary L. Kunz
*Assistant Examiner*—Howard V. Owens
(74) *Attorney, Agent, or Firm*—Fulbright & Jaworski L.L.P.

(57) ABSTRACT

The present invention is directed to compositions and methods for removal of nucleic acid probes from sample nucleic acids, particularly when the sample nucleic acids are attached to a solid support. The invention also concerns methods of stripping and reusing nucleic acid blots.

18 Claims, No Drawings

STRIPPING NUCLEIC ACIDS WITH IODINE AND SODIUM THIOSULFATE

BACKGROUND OF THE INVENTION

1. Field of the Invention

The present invention relates generally to the fields of molecular and cellular biology. More particularly, it concerns compositions and methods for removal of nucleic acid probes from sample nucleic acids, for example, sample nucleic acids attached to a solid support. The invention also concerns methods of stripping and reusing nucleic acid blots.

2. Description of Related Art

The central dogma of molecular biology holds that genetic information flows from nucleic acids (DNA and RNA) to proteins, and that the functions and relative abundances of proteins within a biological system defines that system. Proteins are polymers of amino acids and it is the sequence of amino acids within the polymer that determines the function of the protein. Amino acid sequences are encoded by nucleic acid sequences that exist in domains known as genes that are present in the genomes of biological entities. Genomes are the nucleic acid storehouses of genetic information present in all known living systems.

Genomes are typically composed of DNA, though there are a number of viruses with RNA genomes. The genes in DNA are converted to proteins via an RNA intermediate known as messenger RNA (mRNA). The rate of conversion of a DNA segment composing a gene to mRNA, and the subsequent degradation rate of that mRNA, affects protein production which ultimately impacts the state of that organism. The importance of nucleic acids in biology is unquestioned, thus a substantial amount of research effort has been applied to identifying gene sequence, structure, and function, as well as the relative rates of messenger RNA synthesis and degradation and the abundance of particular mRNA species.

A variety of techniques have been employed in the detection and quantification of both RNA and DNA. Most of these techniques rely on the capacity of nucleic acids to interact in a sequence specific manner known as hybridization. Hybridization occurs when two nucleic acid molecules possessing complementary sequences interact to form a, typically, double helical structure. Hybridization studies designed to identify or quantify a sample nucleic acid possessing a given sequence typically involve synthesizing an isotopically or non-isotopically labeled nucleic acid probe with a sequence that is complementary to the sample nucleic acid to be detected. The labeled nucleic acid probe is incubated with the sample population to allow hybridization between target and probe. Labeled nucleic acids that have not hybridized are removed, leaving the hybridized probe to be detected via the isotopic or non-isotopic label.

Of the many techniques for nucleic acid analysis that rely on hybridization, some involve immobilizing the sample nucleic acid on a solid support. Detection and/or quantification methods that rely on immobilization of RNA or DNA species by physical attachment to a solid support are well-known and include, but are not limited to, Northern (RNA sample nucleic acid), Southern (DNA sample nucleic acid), dot, slot, colony lifts, and related blot analyses (Maniatis et al., 1989), sandwich hybridization (Kwoh et al., 1989), and hybridization of a labeled amplification product to an oligonucleotide attached to a solid support (Woolford and Dale 1992).

In blot analyses, the solid support is usually a membrane and the sample is usually a heterogeneous population of nucleic acids purified from a cell culture, tissue, or organism. UV or chemically induced crosslinking between the sample and membrane generates the sample matrix. Isotopically or non-isotopically labeled probes (nucleic acids possessing sequences complementary to the RNA or DNA to be detected) are synthesized by enzymatic or synthetic means and mixed with the sample matrix. Hybridization of the probe to the subset of nucleic acids with complementary sequences, removal of the non-hybridized probe molecules by extensive washing, and detection of the remaining label provides for the positive identification and quantification of nucleic acids possessing the given sequence.

The sample matrices can be used multiple times, provided that all hybridized probe is removed prior to initiating hybridization of a new probe. The complete removal of the preceding probe is important, as the signal from one probe can affect the detection and quantification of a second nucleic acid. Removing any hybridized nucleic acid requires that sufficient energy be introduced to disrupt all hydrogen bonding and stacking interactions between probe and target. Additionally, the solution must be stringent enough to deny reannealing once the interaction between probe and target has been disrupted. Temperatures that exceed the melting temperature of the probe and target in solutions that lack monovalent salts and include detergents are typically used to remove probes from a solid support (Maniatis et al., 1989). However, in many instances, this level of stringency is inadequate to completely remove the probe leaving residual signal that can affect the subsequent analysis of other targets. In addition, the extreme conditions often cause irreversible damage to the sample matrix, either by removing sample nucleic acids altogether, or altering their chemical properties. These two problems often necessitate that a sample matrix be used one time and then discarded.

Given the time and expense involved in the preparation of a sample matrix, in addition to the fact that some sample matrices would be difficult to reproduce given the unavailability of starting materials (for example, patient samples, etc.), the ability to reuse a sample matrix would represent a significant advance in the art.

SUMMARY OF THE INVENTION

The present invention overcomes the limitations present in the art by providing compositions and methods for removing hybridized nucleic acid probes from sample nucleic acids, for example from sample matrices consisting of sample nucleic acids attached to solid supports. The invention provides for the specific degradation or cleavage of a nucleic acid probe following hybridization and detection, reducing the energy of hybridization between the sample nucleic acid and the various nucleic acid probe molecules. The reduction in hybridization energy provides for complete removal of the nucleic acid probe under conditions that are less likely to affect the sample nucleic acids and/or sample matrix (lower temperature and/or less extreme conditions). The present invention thus provides for the reuse, and even multiple uses, of sample matrices. The present invention also provides kits, including, but not limited to, kits for nucleic acid probe degradation, cleavable nucleic acid probe synthesis, sample matrix stripping and reuse, and nucleic acid detection.

For clarity, the nucleic acid(s) attached to a solid support will be referred to as the sample nucleic acid(s) or target; the solid support plus sample nucleic acid(s) will be referred to as the sample matrix; and the nucleic acid probe (or "probe") will be the nucleic acid molecule that hybridizes to the sample nucleic acid(s).

Various basic aspects of the invention are summarized as follows. Note that, in accordance with long-standing patent law practice and convention, the words "a" and "an" denote "one or more" when used in this application, including the claims. Further, the breaking of a first bond in a nucleic acid probe can occur in conjunction with the breaking of other bonds, and there is no limitation in the invention as to breaking of "one and only one bond."

The invention provides a method of removing a nucleic acid probe from a sample nucleic acid comprising obtaining a sample nucleic acid and a nucleic acid probe, the nucleic acid probe associated with the sample nucleic acid, breaking at least a first bond of the nucleic acid probe, and removing the nucleic acid probe from the sample nucleic acid. Of course, more bonds than a first bond may be broken, and, typically, more than one bond will be broken.

In certain embodiments, the sample nucleic acid probe comprises DNA. In other embodiments, the sample nucleic acid probe comprises RNA. In still other aspects, the nucleic acid probe comprises DNA and RNA.

In embodiments of the present invention, the first bond on the nucleic acid probe is broken via chemical or physical means. The nucleic acid probes of the present invention may be comprised of a variety of different types of degradable phosphate backbone bonds that are broken. In certain aspects of the invention, the bond is a phosphodiester bond. In alternative embodiments, the bond is a phosphorothioate bond. The bond may be broken by an enzyme, exemplified by, but not limited to, uracil DNA glycosylase, a ribonuclease, inosine ribonuclease, deoxyribonuclease, or combinations thereof. As used herein in various embodiments of the present invention, the term "nuclease" will be understood to include ribonuclease, deoxyribonuclease, endonuclease and exonuclease. In other embodiments, the bond is broken by one or more particular wavelengths of light, or by temperature. In further preferred embodiments, the degradable bond of the nucleic acid probe is broken by a combination of two or more of the above methods.

In particular aspects of the invention, the sample nucleic acid comprises DNA. In other aspects, the sample nucleic acid comprises RNA. In certain embodiments, the sample nucleic acid is comprised within a cell. In further embodiments, the sample nucleic acid is comprised within a virus.

In various preferred aspects of the present invention, the sample nucleic acid is attached to a solid support. In certain embodiments, the solid support is a membrane, exemplified by, but not limited to, a nitrocellulose membrane or a nylon membrane. In other embodiments, the solid support is a resin, including, but not limited to, an ion exchange chromatography resin such as an anion or cation exchange resin, or an affinity chromatography resin. In further embodiments, the solid support is plastic, such as a microtiter plate. Other examples of solid supports contemplated for use in the present invention include, but are not limited to, a magnetic bead, glass, or a microchip.

In particular embodiments, the sample nucleic acid is separated by electrophoresis prior to attachment to the solid support. In some embodiments, the sample nucleic acid may be cleaved by an enzyme prior to separation by electrophoresis.

In certain preferred aspects of the invention, the obtaining may be characterized as comprising obtaining a sample nucleic acid, obtaining a nucleic acid probe, and admixing the nucleic acid probe with the sample nucleic acid, for a period of time and under conditions sufficient to allow association of the nucleic acid probe with the sample nucleic acid.

The invention also provides a method of stripping a nucleic acid probe from a sample nucleic acid, the sample nucleic acid attached to a solid support, that may be characterized as comprising obtaining a solid support comprising a sample nucleic acid attached thereto, obtaining a nucleic acid probe, the nucleic acid probe comprising at least a first phosphorothioate bond, admixing the nucleic acid probe with the solid support, for a period of time and under conditions sufficient to allow association of the nucleic acid probe with the sample nucleic acid attached to the solid support, cleaving the phosphorothioate bond of the nucleic acid probe with iodine, removing the nucleic acid probe from the sample nucleic acid, and admixing sodium thiosulfate with the solid support, thereby removing excess iodine from the solid support.

The invention also provides a kit for removing a nucleic acid probe from a sample nucleic acid, comprising in a suitable container a compound that breaks at least a first bond of the nucleic acid probe. In certain aspects, the compound is a chemical, such as iodine. In other aspects, the compound is an enzyme, such as uracil DNA glycosylase, a ribonuclease or a deoxyribonuclease.

In certain embodiments of the kits of the present invention, the kit further comprises at least a first cleavable nucleotide for incorporation into the nucleic acid probe. In particular aspects, the cleavable nucleotide is a phosphorothioate nucleotide. In other aspects, the cleavable nucleotide is a uracil nucleotide. In further embodiments, the cleavable nucleotide is an inosine nucleotide.

Additionally, the present invention provides a kit for removing a nucleic acid probe from a sample nucleic acid, comprising, in a suitable container, probe degradation buffer, and reconstitution buffer. In certain preferred embodiments, the probe degradation buffer comprises iodine.

In other embodiments, the kits of the present invention further comprises, in a suitable container, at least a first cleavable ribonucleoside triphosphate, ATP, CTP, GTP and UTP, RNA polymerase, RNase inhibitor, and transcription buffer. In still other aspects, the kits further comprise, in a suitable container, at least a first cleavable deoxyribonucleoside triphosphate, dATP, dCTP, dGTP, dTTP and DNA polymerase. As used herein in certain aspects of the present invention, the term "nucleotide(s)" will be understood to include ribonucleotide(s) and deoxyribonucleotide(s).

Thus, in a particular embodiment, the present invention also provides a kit for removing a nucleic acid probe from a sample nucleic acid, that may be characterized as comprising, in a suitable container, probe degradation buffer comprising iodine and SDS, reconstitution buffer comprising sodium thiosulfate and SDS, [α-S] CTP, ATP, GTP and UTP, an RNA polymerase selected from the group consisting of SP6 RNA polymerase, T7 RNA polymerase and T3 RNA polymerase, placental RNase inhibitor, and transcription buffer comprising sodium chloride, Tris (pH 8), magnesium chloride, spermidine-HCl, and DTT.

The present invention further provides a kit for detecting the association of a nucleic acid probe with a sample nucleic acid, comprising in a suitable container a solid support and a compound that breaks at least a first bond of the nucleic acid probe.

Components of the above-summarized particular aspects of the invention will be discussed in detail below. Of course, this invention is in no way limited to the particular embodiments of the invention summarized herein. Rather, the disclosure of this specification is more than adequate to enable the full scope of the invention to those of skill.

I. Nucleic Acid Probes

The nucleic acid probes used in most detection methods hybridize to their targets, typically, over regions in excess of one hundred nucleotides, although this length is not always required. The hybridization energy of long stretches is significant and requires substantial energy to disrupt. Breaks introduced in the polynucleotide chain of the probe molecule effectively reduce the energy required to disrupt interactions between probe and target by reducing the size of the regions of interaction. For instance, a probe that is 500 nucleotides long can be reduced to a series of polymers 5–10 nucleotides in length by periodically cleaving phosphodiester bonds along the polynucleotide backbone. "Melting temperature" is a temperature that will cause hybridization of nucleic acids of a particular length to disassociate.

The melting temperature for an average ten nucleotide long probe is less than 50° C., whereas that of a 500 nucleotide long probe exceeds 100° C. Owing to this change in melting temperature, removing the short polymers from a target requires a relatively non-stringent wash of 50–60° C., whereas boiling the sample matrix is often insufficient to remove a 500 nucleotide long probe. The specific degradation of the probe reduces the stringency required to remove the probe from a sample matrix and enhances its complete removal, thus facilitating the multiple usage of the sample matrix.

A. Size and Composition

Nucleic acid probes used for detecting targets attached to a solid support are typically 100 to 5,000 nucleotides long, although probes as short as ten nucleotides to probes as large as 1,000,000 nucleotides can be used provided appropriate conditions. The present invention thus also contemplates the use of nucleic acid probes of any intermediate length, including, but not limited to, probes of 20, 30, 50, 75, 150, 200, 300, 500, 600, 800, 1000, 2500, 7000, 10,000, 50,000, 100,000, 250,000, 500,000 or 750,000 nucleotides in length. The present invention involves cleaving the probe at positions held by a particular nucleotide (for instance, cytidine), so that, regardless of size, the probe is reduced to constituent fragments that can be easily removed from the sample matrix. Nucleic acid probes are typically composed of RNA or DNA, although a probe comprising both RNA and DNA could also be used. The invention is applicable for probes of each these compositions.

Another nucleic acid molecule that is contemplated for use as a probe is a peptide nucleic acid (PNA). PNAs can be used as degradable probes. PNA probe removal can be facilitated by digestion with a protease that would degrade the peptide bonds of the backbone without affecting the nucleic acids attached to the solid support. The resulting peptide nucleic acid fragments can be easily removed by a mild wash.

B. Degradable Probes Several methods exist for producing nucleic acids that are more labile under a given set of conditions. These can be employed in the invention. Applications for specifically degradable nucleic acids have been described in the literature. In the few cases where the described use for the technology is probing a nucleic acid on a solid support, the purpose for cleaving the probe is to release the reporter into the solution to enhance the sensitivity of the assay and to avoid background caused by non-specific interactions of probe with the solid support (Urdea, 1995; Urdea and Horn, 1995; Urdea and Horn, 1996a; Urdea and Horn, 1996b). Other applications for making specifically degradable nucleic acids are cloning (Mag et al., 1991; Rashtchian and Berninger, 1992); producing amplification products that can be specifically degraded following detection to decrease the risk of contamination (Longo et al., 1990; Frasier et al., 1996); analyzing therapeutic oligonucleotides (Wyrzykiewicz, U.S. Pat. No. 5,629,150); sequencing (Gish and Eckstein, 1988); and footprinting interactions of molecules with nucleic acids (Schatz et al., 1991). These degradable probe technologies apparently have not been used to facilitate the stripping of blots.

Effective degradable nucleic acid probes typically share several characteristics. The element of the probe that confers cleavage should not significantly affect the hybridization kinetics, energy, or specificity between the probe and target. The degradation reaction advantageously occurs regardless of whether the probe is hybridized to a complementary sequence. The level of degradation should be sufficient to reduce nucleic acid polymers of hundreds or thousands of nucleotides to polymers of smaller size, typically less than one hundred nucleotides. The reagents and wash conditions required to degrade and remove the probe from the sample matrix should have minimal impact on the sample nucleic acid or its associate with a solid support.

Methods for the specific degradation of nucleic acid probes are exemplified by but not limited to: enzymatic degradation resulting from specific recognition of the probe but not the sample nucleic acid; chemical degradation resulting from the presence of chemical groups in the probe that react with agents added to a sample matrix that result in strand scission of the probe but not sample nucleic acid; light or temperature induced degradation resulting from the presence of chemical groups in the probe that are activated by light or extreme temperatures to cause strand scission of the probe but not the sample nucleic acid; and combinations of any two or more methods, for example the combination of enzymatic and chemical degradation.

In some embodiments, the internucleotide phosphates of RNA or DNA can be modified by replacing one of the non-bridging oxygens with a phosphothiol or phosphodiester bond. Such modification has little effect on the hybridization characteristics of the molecule but has a significant impact on its chemistry. Thiol-modified phosphates (phosphorothioates) react with iodine and related reagents to cause strand scission of the modified nucleic acids (Gish and Eckstein, 1988). Thus the existence of phosphorothioates within a nucleic acid (RNA or DNA) can provide a method for the specific reduction of that nucleic acid to smaller polymers.

In embodiments where the nucleic acid probe comprises at least a first phosphorothioate bond, the bond may be broken by a chemical, such as iodine. In certain aspects, the concentration of the iodine is between about 5 $\mu$M and about 500 mM. In preferred embodiments, the concentration of the iodine is between about 0.1 mM and about 25 mM. In more preferred embodiments, the concentration of the iodine is between about 0.5 mM and about 2 mM. While the concentrations of iodine employed to break a phosphorothioate bond are described in discrete ranges, it will be understood by the person of ordinary skill in the art that intermediate ranges of iodine concentration are also encompassed within these ranges. Thus, the iodine concentration may be between about 5 $\mu$M and about 250 mM, between about 25 $\mu$M and about 500 mM, between about 50 $\mu$M and about 100 mM, about 0.1 mM and about 10 mM, between about 0.2 mM and about 25 mM, between about 0.25 mM and about 5 mM, between about 0.5 mM and about 1 mM, between about 1 mM and about 2 mM, or between about 0.75 mM and about 1.5 mM.

Additional methods exist for producing nucleic acids that are particularly susceptible to degradation under specific conditions. These can be incorporated into the invention. For example, the enzyme uracil DNA glycosylase removes the uracil base from the sugar-phosphate backbone, leaving an abasic site. This abasic site is recognized and cleaved by certain nucleases, for example, Exonuclease IV (Rashtchian and Berninger, 1992) and Exonuclease I (Brody, 1991) from *E. coli*. Thus, the combination of uracil DNA glycosylase and an appropriate nuclease serves to cleave the phosphodiester backbone of nucleic acid probes which have uridine incorporated therein. The abasic sites created by the action of uracil DNA glycosylase can also be cleaved by acid or base hydrolysis. Thus the combination of enzymatic and chemical methods are also contemplated for use in cleaving nucleic acid probes.

In one aspect of the present invention, the nucleic acid probe comprises at least a first uracil residue. Nucleic acid probes comprising one or more uracil residues may be broken by a combination of uracil DNA glycosylase and an exonuclease, or in alternate aspects, by a combination of uracil DNA glycosylase and a chemical that promotes either acid hydrolysis by lowering the pH, for example to a pH value below a neutral pH, including, but not limited to, a pH of 6, 5, 4, 3, 2, 1 or 0, and intermediate values thereof, or base hydrolysis by raising the pH, for example to a pH value above a neutral pH, including, but not limited to, 8, 9, 10, 11, 12, 13 or 14, and intermediate values thereof. In particular embodiments of the present invention, the bond is broken by a hydroxyl ion. In certain aspects, the concentration of the hydroxyl ion is between about 1 M and about $10^{-6}$ M. In preferred embodiments, the concentration of the hydroxyl ion is between about $10^{-1}$ M and about $10^{-5}$ M. In more preferred embodiments, the concentration of the hydroxyl ion is between about $10^{-3}$ M and about $10^{-5}$ M. It will be understood by the person of ordinary skill in the art that intermediate ranges or values of hydroxyl ion concentration are also encompassed within these ranges.

Also, inosine RNase can be used to cleave RNA probes at positions occupied by inosine (Scadden and Smith, 1997). Additionally, RNA probes are labile in solutions possessing elevated hydroxyl levels (pH of about 9 or above) or ribonucleases, including, but not limited to, ribonuclease A, ribonuclease B, ribonuclease C, ribonuclease S, ribonuclease $T_1$, ribonuclease $T_2$, ribonuclease $U_1$ and ribonuclease $U_2$ (all of the above ribonucleases are available commercially, for example from Sigma Chemical Company, St. Louis, Mo.). Similarly, DNA probes can be degraded by deoxyribonucleases, including, but not limited to, deoxyribonuclease I and deoxyribonuclease II (all of the above ribonucleases are available commercially, for example from Sigma Chemical Company, St. Louis, Mo.). All of the above can be used within the scope of the invention.

Photolabile groups that can be incorporated to provide nucleic acid probes that are degraded by specific light emissions are provided in U.S. Pat. No. 5,430,136 (incorporated herein by reference in its entirety). Such photolabile groups also can be incorporated into the invention.

C. Preparation of Degradable Probes

Methods for the specific degradation of nucleic acid probes are exemplified by, but not limited to: enzymatic RNA synthesis by transcription, primer extension, replication, or non-templated polymerization that incorporates nucleotides that are labile under defined conditions for the purpose of specific degradation of the probe molecule, for example using SP6 RNA polymerase (Green et al., 1983) or T7 RNA polymerase (Tabor and Richardson, 1985); enzymatic DNA synthesis by primer extension, promoter-driven polymerization, or non-templated polymerization that incorporates nucleotides that are labile under defined conditions for the purpose of specific degradation of the probe molecule, for example by nick-translation (Kelly et al., 1970) or random priming (Feinberg and Vogelstein, 1983); chemical synthesis of RNA, DNA, or similar molecules that possess chemical groups that are labile under defined conditions for the purpose of specific degradation of the probe molecule (reviewed in Caruthers et al., 1987); and post synthesis modification of a nucleic acid probe by chemical, photochemical, or enzymatic means to introduce changes that are labile under defined conditions for the purpose of specific degradation of the probe molecule.

The preparation of specifically degradable nucleic acid can be accomplished by a variety of methods. Nucleotides and their analogs can be incorporated by RNA and DNA polymerases to provide nucleic acids with labile sites. RNA and DNA possessing labile nucleotides can also be chemically synthesized using phosphoramidites. Labile sites can even be introduced to RNA or DNA molecules following enzymatic or chemical synthesis. For example, adenosine deaminase converts adenosines to inosines within a nucleic acid molecule (Hough and Bass, 1994). This conversion effectively converts an otherwise stable RNA into a substrate for inosine ribonuclease providing an avenue for the specific destruction of the nucleic acid (Scadden and Smith, 1997).

D. Detectable Labels

Labeled nucleic acids are used to visualize the hybridized product that reveals the presence and/or amount of a target molecule. The label can be a radioisotope, an enzyme, or a fluorescent, chemiluminescent, or bioluminescent molecule. The labels can be either a component of the nucleotide (especially radioisotopes), covalently attached to a nucleotide, or attached to the nucleotide via a binding agent (for instance, an enzyme-linked antibody bound to a nucleic acid). The labeled nucleotide(s) can either be part of the region of the nucleic acid probe that hybridizes to the sample nucleic acid, or be part of a nucleic acid probe region that is not complementary to the sample nucleic acid. The label is preferably a part of the nucleic acid probe, but in certain embodiments, such as sandwich hybridization, the label can be incorporated into a distinct nucleic acid molecule that binds to a nucleic acid probe, particularly when the nucleic acid probe is hybridized to a sample nucleic acid attached to a sample matrix.

The detectable labels contemplated for use in the present invention are exemplified by, but not limited to: radioactive labels, such as tritium, carbon-14, phosphorus-32 or phosphorus-33 or sulfur-35; enzymatic labels, such as alkaline phosphatase or horseradish peroxidase; fluorescent labels, such as green fluorescent protein (GFP), rhodamine, fluorescein isothiocyanate, phycoerythrin, phycocyanin, allophyocyanin, o-phthaldehyde, fluorescamine, Texas Red or renographin; chemiluminescent labels, such as acridinium salt, isoluminol, imidazole, theromatic acridinium ester, luminol, or oxalate ester; bioluminescent labels, such as aequorin, luciferin, or luciferase; or metal labels, such as gold.

II. Sample Nucleic Acids

A. Size and Composition

Typical size ranges for nucleic acids attached to a solid support to generate the sample matrix are 8 to 20,000 nucleotides, though entire chromosomes (comprising approximately $10^9$ base pairs) have been assayed using immobilization methods. The present invention thus also contemplates the use of sample nucleic acids of any intermediate length, including, but not limited to, 9, 10, 12, 15, 20, 30, 50, 75, 150, 200, 300, 500, 600, 800, 1000, 2500, 7000, 10,000, 50,000, 100,000, 250,000, 500,000, 750,000, $10^6$, $5 \times 10^6$, $10^7$ or $10^8$ nucleotides in length. RNA and DNA in both single and double-stranded form can be used as the sample. Though purification is often a prerequisite for attachment to a solid support (for example Northern and Southern blotting, dot/slot blots, etc.), many methods actually utilize unpurified nucleic acids (for example colony or plaque lifts, in situ hybridization, etc.).

B. Sources

Virtually any source of nucleic acid can form a sample for immobilization in the creation of a sample matrix. Single-stranded and double-stranded RNA and DNA purified (either together or separately) from prokaryotic, eukaryotic, or viral sources can all be used. In addition, nucleic acids from in vitro enzymatic reactions or chemical syntheses can likewise be affixed to a solid support to form the sample matrix. Those of skill will be able to determine appropriate sources of such acceleration.

C. Isolation Methods

There are numerous methods known to those of skill for isolating nucleic acids from biological sources (reviewed in Maniatis, 1989). DNA and RNA isolation is routinely accomplished by homogenizing a sample to release all cellular or capsid components into solution. The nucleic acids are then purified away from the contaminating lipids, proteins, and small molecules by preferential binding to a solid support, organic extraction, or differential precipitation.

III. Solid Supports

Many different examples of solid supports for use in attachment of sample nucleic acids are known to those of skill in the art. The methods used in the attachment of sample nucleic acids to solid supports is also well known and understood by those of skill in the art (Maniatis et al., 1989; Ausubel et al., 1989).

A. Membranes

Nitrocellulose, nylon and cellulose are the most common membranes used for immobilizing DNA and RNA in analyzing samples by Northerns, Southerns, dot/slot blots, and colony/plaque lifts. Nitrocellulose is thought to immobilize nucleic acids through hydrophobic and electrostatic interactions. Baking a blotted sample can be used to increase the strength of the interaction between the nitrocellulose and the nucleic acid sample. Nylon membranes are charged providing extensive electrostatic interactions with the phosphate backbone of both RNA and DNA. UV irradiation and baking or drying can be used to actually cross-link activated groups on the membrane to the nucleic acids in the sample. Those of skill know a variety of other methods and technologies for affixing nucleic acids to membranes, including, but not limited to, chemical interactions, protein/chemical interactions, protein/protein interactions and sugar trans-esterification.

B. Other Solid Supports

Resins, plastics, magnetic beads, glass, and microchips can also be used as the solid support in certain embodiments of the present invention. The supports may be derivatized to include chemical moieties that will interact with RNA or DNA to provide immobilization through electrostatic or hydrophobic interactions, covalent attachment (Fodor et aL, 1991), or by protein or small molecule interactions between a molecule attached to the nucleic acid sample (such as streptavidin) and a molecule attached to the solid support (such as biotin) (Huang et al., 1996).

IV. Hybridization Methodology

Methods for using the degradable nucleic acid probes of the present invention are exemplified by, but not limited to: Northern blots; Southern blots; dot/slot blots; colony/plaque lifts; ELISAs; using sample nucleic acids as templates, to synthesize probes that can be hybridized to and easily removed from nucleic acids attached to a solid support; and sandwich hybridization schemes where the degradable nucleic acid hybridizes to a polynucleotide attached to a solid support and a second polynucleotide that possesses a detectable label. Of course, many modifications of these procedures are known to those of skill and contemplated by the invention.

A. Southern Blot

DNA may be size fractionated by electrophoresis through a gel, typically agarose, then transferred and immobilized on a membrane in such a manner that the relative positions of the fractionated DNA fragments are maintained (Southern, 1975). The resulting blot can then be mixed with a nucleic acid probe to identify the subset of the DNA population that possesses a sequence that is complementary to the probe.

B. Northern Blot

RNA (especially messenger RNA) may be size fractionated by electrophoresis through a gel, typically agarose then transferred and immobilized on a membrane in such a manner that the relative positions of the fractionated RNA are maintained (Alwine et al., 1977). The resulting blot can then be mixed with a nucleic acid probe to identify the subset of the RNA population that possesses a sequence that is complementary to the probe.

C. Dot/Slot Blot

An RNA or DNA sample is spotted onto a membrane and immobilized. The spotting of the sample can either be done by simply dropping an aliquot onto the membrane (Kafatos et al., 1979), or using a filtration device to spot the nucleic acids in a fixed pattern (Brown et al., 1983). The dot or slot blot is incubated with a nucleic acid probe to allow hybridization between the probe and target molecules on the blot possessing sequences complementary to the probe. Removal of non-hybridized probe and detection of the remaining label provide identification and quantification of the target molecules.

D. Colony/Plaque Lifts

Bacterial and other colonies as well as viral plaques can be grown on solid media, producing clonal populations of an organism. In a typical colony or plaque lift, the nucleic acids from the clones are transferred to a membrane by lysing the colony/plaque and placing a membrane on top of the medium (Grunstein and Hogness, 1975). The RNA/DNA adsorbs to the membrane and is subsequently immobilized generating a colony or plaque blot. A probe is introduced to the blot and hybridization reveals those colonies or plaques possessing RNA or DNA that is complementary to the added probe.

E. Sandwich Hybridization

Sandwich hybridization schemes involve attaching a sample nucleic acid, typically a synthetic oligonucleotide, to a solid support. The sequence of the attached nucleic acid is designed to be complementary to the sequence of a nucleic acid probe molecule to be detected and/or quantified out of a population of nucleic acids. A sample population is then incubated with the oligonucleotide/solid support sample matrix. Non-hybridized members of the sample population are removed. A labeled nucleic acid whose sequence is complementary to another portion of the nucleic acid probe molecule is added and allowed to hybridize. Non-hybridized, labeled nucleic acid is removed leaving only the labeled nucleic acid that is hybridized to those nucleic acid probe molecules that are themselves hybridized to the sample matrix. The label is then detected, providing an estimate of the amount of a nucleic acid probe molecule in nucleic acid population.

F. In situ Hybridization

In situ hybridization provides a method for the morphological localization of RNA or DNA molecules of a given sequence (reviewed in Hofler et al., 1988). Sections or whole mounts of an organism are fixed to preserve tissue and cellular morphology (this includes immobilizing nucleic acids within the sample). A probe is mixed with the preserved tissue. Hybridization and detection identifies locations within the organism, tissue, or cell that house RNA or DNA molecules possessing sequences complementary to the probe.

G. Reverse Blots

Reverse blots differ from those described above in that nucleic acids of a single sequence are attached to a solid support to yield the sample matrix and the heterogeneous population serves as the probe. The heterogeneous population may be labeled, either directly by chemical means or enzymatically by second strand synthesis incorporating modified nucleotides. The labeled population is incubated with the sample matrix and the non-hybridized, labeled molecules are removed by washing. The hybridized molecules are then detected, providing for the positive identification of those nucleic acids within the population that possess a given sequence.

A related technique is used to detect the nucleic acid products of an amplification reaction such as PCR™. In this detection scheme, the sample matrix consists of a solid support (beads, microtiter plates, and microchips are a few of the supports that have been used) covalently attached to oligonucleotides (or polynucleotides) possessing a sequence that is complementary to the target amplification product. One skilled in the art will appreciate that there are a variety of detection methods. In a commonly used strategy, a labeled nucleotide is incorporated during the amplification reaction, providing labeled nucleic acids that will serve as probes. The double stranded nucleic acid amplification products are dissociated, mixed with the sample matrix, and incubated. Non-hybridized molecules are washed from the solid support, leaving the labeled, hybridized amplification products for detection.

V. Kits

All of the essential materials and reagents required for the various aspects of the present invention may be assembled together in a kit. A variety of kits are contemplated, including, but not limited to, nucleic acid probe degradation kits, degradable nucleic acid probe synthesis kits, blot stripping and reuse kits, nucleic acid detection kits as well as combinations of any or all of the above into larger combination kits.

The container means will generally include at least one vial, test tube, flask, bottle or other container means, into which, for example, the nucleic acid probe removal or synthesis formulations are placed, preferably, suitably allocated or aliquoted.

When the components of the kit are provided in one or more liquid solutions, the liquid solution preferably is an aqueous solution, with a sterile aqueous solution being particularly preferred. The components of the kit may also be provided in dried or lyophilized forms. When reagents or components are provided as a dried form, reconstitution generally is by the addition of a suitable solvent. It is envisioned that the solvent also may be provided in another container means. The kit may have a single container means, or it may have distinct container means for each compound. In certain aspects, one or more solid supports used for attaching either sample or probe nucleic acids are also provided.

The kits of the present invention also will typically include a means for containing the components in close confinement for commercial sale such as, e.g., injection or blow-molded plastic or cardboard containers into which the desired components are retained. Additionally, instructions for use of the kit components is typically included.

Components for an RNA probe synthesis and degradation kit may include, but are not limited to, an RNA polymerase, such as SP6 RNA polymerase, T7 RNA polymerase, or T3 RNA polymerase, and a ribonuclease inhibitor, such as placental ribonuclease inhibitor, antibodies to ribonucleases that inhibit their activity or small molecule ribonuclease inhibitors, such as uridine-vanadate, 2' CMP, 2' UMP or oxyvanadium IV.

DESCRIPTION OF ILLUSTRATIVE EMBODIMENTS

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

RNA Probes Hybridized to Northern Blots

Standard and phosphorothioate RNAs possessing a sequence complementary to that of the mouse β-actin mRNA were synthesized by transcription using T7 RNA polymerase. Parallel 20 μl transcription reactions of 40 mM Tris-HCl (pH 8.0), 20 mM NaCl, 6 mM MgCl$_2$, 2 mM spermidine HCl, 10 mM DTT, 0.5 μg template DNA, 5 U of T7 RNA polymerase, 0.5 M ATP and GTP, 3 μM [α-$^{32}$P]UTP, and either 0.5 M CTP or 0.5 M C[α-thio]TP. The reactions were incubated for thirty minutes at 37° C. The reactions were removed, TCA precipitated (Maniatis et al., 1982), and the transcription products analyzed by scintillation counting. Based on TCA precipitable counts, the modified CTP supported transcription as effectively as the natural CTP. Aliquots from the reactions were analyzed by polyacrylamide gel electrophoresis to confirm that the majority of the transcription products were full-length. These results illustrate that modified RNAs can be effectively produced by enzymatic synthesis.

Three and one microgram aliquots of mouse lung RNA were fractionated via electrophoresis on a formaldehyde/1% agarose gel. The fractionated RNA was blotted onto a positively charged membrane by downward alkaline transfer. The resulting Northern blot was stored at −20° C. 10$^6$ cpm of the phosphorothioate and standard mouse β-actin RNA probes described above were mixed with the Northern blots of mouse lung RNA that had been pre-equilibrated with hybridization buffer (50% formamide, 375 mM NaCl, 37.5 mM trisodium citrate, 7% SDS, and 100 μg/ml yeast RNA). Following overnight incubation at 68° C. in hybridization buffer, non-hybridized probe was removed by successive 15 minute washes of 300 mM NaCl, 30 mM trisodium citrate, 0.1% SDS and 15 mM NaCl, 1.5 mM trisodium citrate, 0.1% SDS at 68° C. The probe hybridized to β-actin was visualized via autoradiography, revealing that both probes produced approximately equivalent signals from identical amounts of target.

The Northern blots were then subjected to a ten minute wash of 0.5 mM iodine/0.1% SDS at 55° C. and a ten minute wash of 5 mM sodium thiosulfate/0.1% SDS at 55° C. The sodium thiosulfate wash was used to remove any iodine that remained in the blot. Hybridized probe on the two Northern blots were visualized by autoradiography, revealing that the thiol modified probe was removed while the standard probe was still present. Removal of the standard probe was then attempted by adding boiling 0.1% SDS to the Northern blot and autoclaving the Northern blot in 0.1% SDS. Autoradiography following both treatments revealed that the standard probe could not be removed from the blot.

The iodine-treated blot was reprobed by an RNA probe specific to the murine GAPDH mRNA by the protocol described above. Autoradiography resulted in a signal from a distinct band on the membrane, indicating that the iodine treatment had not altered the sample matrix in a way that affected the detection of additional targets.

EXAMPLE 2

DNA Probes Hybridized to Northern Blots

A DNA fragment corresponding to an internal region of the murine gene encoding GAPDH was denatured by heating to 95° C. The DNA (25 ng) was added to a solution of 0.1 μg/μl random sequence decamers (ten nucleotide long oligonucleotides), 100 mM Tris-HCl (pH 7.0), 10 mM $MgCl_2$, 1 mM DTT, 100 μM dGTP, 100 μM dTTP, 100 μM dCTP or (α-thio)dCTP, and 3 μM [α-$^{32}$P] dATP. 5 U of the Klenow fragment of $E.$ $coli$ DNA polymerase and sufficient nuclease-free water to bring the final volume of the reaction up to 20 μl were added and the reaction was transferred to a 37° C. incubator for ten minutes. The reactions were stopped by the addition of 1 μl of 0.5 M EDTA. The extension products were analyzed by scintillation counting following TCA precipitation (Maniatis et al, 1982). The modified dCTP supported primer extension almost as well as the standard dCTP, indicating that modified DNA can be effectively produced by a DNA dependent DNA polymerase.

Northern blots identical to those in Example 1 were used to test the usefulness of modified DNA probes. $10^6$ cpm of the thiol-modified and unmodified probes to mouse GAPDH described above were mixed with mouse RNA Northern blots that had been pre-equilibrated with hybridization buffer (see Example 1). Following overnight incubation at 42° C., non-hybridized probe was removed by successive 15 minute washes of 300 mM NaCl, 30 mM trisodium citrate, 0.1% SDS and 15 mM NaCl, 1.5 mM trisodium citrate, 0.1% SDS at 42° C. The probe hybridized to β-actin was visualized via autoradiography, revealing that both probes produce equivalent signals from identical amounts of target.

The Northern blots were then subjected to a ten minute wash of 0.5 mM iodine/0.1% SDS at 55° C. and a ten minute wash of sodium thiosulfate/0.1% SDS at 55° C. Hybridized probe on the two Northern blots were visualized by autoradiography, revealing that the thiol modified probe was removed while the standard probe was still present. Removal of the standard probe was then attempted by adding boiling 0.1% SDS to the Northern blot and autoclaving the Northern blot in 0.1% SDS. Autoradiography following both treatments revealed that the standard probe could be removed only by the higher stringency method.

EXAMPLE 3

Probing Dot Blots with Phosphorothioate Probes

Mouse liver RNA (2 μg) was spotted onto multiple squares of positively charged nylon membrane. The RNA samples were crosslinked to the solid support by UV irradiation. The dot blots were probed with standard and phosphorothioate RNA probes specific to the murine β-actin mRNA as described in Example 1. Autoradiography was used to detect the hybridized probes. As with the Northern blots, there was very little difference in signal produced by hybridization of the standard and modified RNA probes.

The blots were then subjected to 55° C. iodine (0.5 mM) and sodium thiosulfate (5 mM) washes. Autoradiography revealed that the phosphorothioate probe had been removed, while most of the signal from the standard RNA probe still remained. A single, five minute wash of boiling 0.1% SDS was then applied to the blot that had been probed with the unmodified RNA. Autoradiography revealed that the probe still had not been completely removed. As with Example 1, these data reveal the utility in using degradable probes as they facilitate multiple usage of blots.

EXAMPLE 4

Probing Southern Blots with Phosphorothioate Probes

Human genomic DNA (10 μg) was digested by 20 U EcoRI for four hours at 37° C. in a 100 μl solution of 100 mM Tris-HCl (pH 7.5), 50 mM NaCl, 10 mM $MgCl_2$, and 0.025% Triton X-100. The DNA was fractionated by electrophoresis on a 0.7% agarose gel. The fractionated DNA was transferred to a positively charged nylon membrane and UV-crosslinked by standard methods. The resulting Southern blot was probed with a phosphorothioate modified RNA probe specific to the human gene encoding β-actin. Autoradiography confirmed the positive identification of the β-actin gene fragment.

The probe was then removed by iodine treatment as outlined in Example 1. Following autoradiography to confirm that the probe had been removed, a standard RNA molecule was used to probe the same gene. Following detection, removal of the probe by iodine washing and subsequently adding boiling 0.1% SDS was insufficient to completely remove the radiolabel. This illustrates the advantage of using a degradable nucleic acid for the detection of DNA targets attached to a solid support.

EXAMPLE 5

Comparison of the Effects of Low and High Stringency Probe Removal Protocols on RNA Dot Blots Identical dot blots were prepared by spotting 2 μg of mouse liver RNA onto positively charged, nylon membranes. One set of blots were subjected to multiple cycles of successive 55° C. washes of 0.5 mM iodine and 5 mM sodium thiosulfate (as described above), and a second set was subjected to multiple rounds of five minute washes in 0.1% SDS. The boiling 0.1% SDS wash is typically used for removing standard DNA probes from Northern and Southern blots (Maniatis et al., 1982). Following the wash cycles, the blots were probed overnight at 68° C. with RNA probes specific to the murine β-actin mRNA. Washing and autoradiography revealed no significant decrease in signal between blots that had been subjected to three and six iodine washes, whereas those that had been subjected to boiling SDS washes displayed significant reductions in signal with increasing numbers of washes. These data illustrate the utility in using the degradable probes, as the reduced stringency of probe removal extends the life span of the blots.

EXAMPLE 6

Reverse Dot Blot using Phosphorothioate cDNA

Reactions comprising 1 μg of total plant RNA with 1 ng of IL-6 human RNA, 0.1 μg/μl random sequence decamers, 50 mM Tris-HCl (pH 8.3), 75 mM KCl, 3 mM $MgCl_2$, 5 mM DTT, 10 U MMLV RT, 250 μM dGTP, 2.5 μM [α-$^{32}$P]dATP, and 250 μM dCTP and dTTP or 250 μM (α-thio)dCTP and (α-thio)dTTP were incubated for 60 minutes at 42° C. The extension products were analyzed by scintillation counting following TCA precipitation. The modified dNTPs supported reverse transcription almost as effectively as the standard dNTPs, indicating that modified DNA can be effectively produced by an RNA dependent DNA polymerase.

cDNA probes of a specific sequence were detected by probing a positively charged nylon membrane that had been spotted and UV crosslinked to an in vitro transcribed, sense strand fragment of the IL-6 gene from human. The level of mRNA specific to the IL-6 gene was measured relative to the amount of signal resulting from hybridization of the labeled cDNA to the target attached to the solid support. Membranes probed by both the phosphorothioate and standard cDNA were subjected to ten minute washes at 55° C. of 0.5 mM iodine in 0.1% SDS and 5 mM sodium thiosulfate in 0.1% SDS. Autoradiography revealed that the phosphorothioate probe had been completely removed, whereas most of the counts from the standard cDNA still remained. The blot that had been probed with the phosphorothioate cDNA could be used to quantify the same message in a second population, because there would be no residual signal from the previous probing. The signal remaining from the standard probe would cause problems in quantifying any subsequent populations. This points to the advantage of having an efficient system for completely removing a hybridized probe from a sample matrix.

EXAMPLE 7

Microchip Arrays and the Use of Phosphorothioate Probes

A relatively new technology uses sample matrices consisting of nucleic acids of defined sequence being immobilized on a derivatized solid support referred to as a chip. An array is formed by immobilizing a diverse sequence pool of nucleic acids on the chip, grouping those molecules bearing identical sequences in distinct locations referred to as addresses (Chee et al., 1996). Hybridization between a set of probe molecules and those nucleic acids attached to the chip can confirm the presence of a target in the probe population as well as providing information on the relative abundance of that molecule. Because constructing chips with attached nucleic acid is so expensive, the capacity to use the sample matrices multiple times is of paramount importance to the ultimate success of the technology. Incorporating specifically degradable probes provides a method by which the life spans of the chips can be extended.

For example, the probe population may be synthesized by transcribing templates derived from a library of the human mitochondrial genome (Chee et al., 1996). The transcripts are labeled by incorporating a fluoresceinated NTP. Phosphorothioate modified RNA is produced by replacing one of the remaining NTPs in the transcription reaction with a phosphorothioate NTP. The resulting probe molecules are hybridized as described (Chee et al., 1996). Following detection, the phosphorothioate probes are degraded by an iodine wash and removed by a low stringency wash. The complete removal of the probe molecules under low-stringency conditions allows the microchip to be used again to assay a new population.

EXAMPLE 8

Sandwich Hybridization Using Phosphorothioate Nucleic Acids

Sandwich hybridization schemes decrease the likelihood of false-positive results by requiring the hybridization of a target molecule to two different nucleic acids. Sandwich hybridization assays can also incorporate degradable nucleic acids into the protocols. Nucleic acids in a sample are used as templates for the synthesis of degradable, complementary sequence DNAs by including [α-thio]dNTPs in the second strand synthesis reactions. Hybridization of the resulting target molecules to nucleic acids attached to a solid support and to labeled nucleic acids provides detection of molecules containing the two sequences. The phosphorothioate-modified DNAs are then degraded by the addition of iodine and removed by a low temperature wash. The advantage to incorporating cleavable molecules into the detection protocol is that the complete removal of hybridized probe allows the costly sample matrices to be used multiple times without significant loss in signal.

EXAMPLE 9

Hybridization of Phosphorothioate Amplification Products for Detection and Quantification Nucleic acid amplification schemes are being included in an increasing number of detection schemes. Hybridization of the amplification products to oligonucleotides attached to a solid support simplifies the detection process. Incorporating phosphorothioates into the amplification products significantly improves the existing technology by reducing the stringency required to remove hybridized probes and thus prolonging the useful life span of the sample matrix. [α-thio] dNTPs are efficiently incorporated by Taq polymerase (Nakamaye et al., 1988), thus replacing standard dNTPs with the modified dNTPs yields phosphorothioate amplification products. Following hybridization and detection of the amplification products, the phosphorothioate nucleic acids are removed by a low temperature iodine wash. A brief sodium thiosulfate wash to remove the residual iodine is sufficient to prepare the sample matrix for a new round of detection. Complete removal of the probe molecules coupled with the ability to remove the probe under relatively non-stringent conditions facilitates the multiple usage of the sample matrices.

EXAMPLE 10

Base Hydrolysis of RNA Probes

Standard RNA probes specific to the β-actin gene were transcribed and used to probe two identical Southern blots as described in Example 4. Following autoradiography to confirm that the signal from the two blots were equivalent, one blot was subjected to a 5 minute wash of boiling 0.1% SDS, while the second was washed 5 minutes with 0.1 M sodium hydroxide at 68° C. The two blots were subjected to autoradiography revealing that the boiling SDS wash was ineffective at removing the probe whereas the sodium hydroxide wash completely removed the signal from the second blot.

The second blot and a Southern blot that had been identically prepared but not probed or washed were mixed with an RNA probe specific to the murine GAPDH gene. Hybridization, washes, and autoradiography as described in Example 4 revealed that the two blots generated similar signals suggesting that the sodium hydroxide wash had no adverse affect on the sample population. These results show that alternative methods to iodine-mediated degradation of phosphorothioates can be used to facilitate the removal of an RNA probe hybridized to a sample matrix.

EXAMPLE 11

UDG Degradation of Uracil-Modified DNA Probes

DNA probes are prepared as described in Example 2, except that phosphorothioate dNTPs are not incorporated and one reaction substitutes 100 μM dUTP for dTTP. The standard and uridine modified DNA molecules are used to probe dot blots prepared as described in Example 8. Hybridization and wash protocols described in Example 8 are followed. Both probe types yields similar signals.

Uracil DNA glycosylase at a concentration of 1 U/ml in a 10 ml solution of 50 mM HEPES-KOH (pH 7.4), 10 mM NaCl, 1 mM EDTA, and 1 mM DTT is incubated for one hour at 37° C. with the dot blots that are probed with standard and uridine DNA probes. The blots are then washed with 0.1% SDS for ten minutes at 55° C. The uridine-modified probes are completely removed, whereas much of the standard DNA probe remains.

EXAMPLE 12

Use of the StripEZ™ RNA Probe Kit

This example describes the use of a specific embodiment of a kit for the synthesis of a degradable ribonucleic acid probe, the hybridization of the degradable ribonucleic acid probe to sample ribonucleic acids on a Northern blot, detection of the hybridized ribonucleic acid probe, and removal of the hybridized ribonucleic acid probe from the sample ribonucleic acids on the sample matrix to allow the blot to be used again. Those of skill in the art will realize that other applications for the probes will necessitate that the sample matrix be created differently and in many cases will require that the probe synthesis reaction be changed, but the overall methodology for creating and using the probes can be maintained in other applications as described in detail herein above.

I. Synthesis of Degradable Probe by in vitro Transcription
   A. Preparation of Template DNA
   RNA probes are produced by the in vitro transcription of DNA templates. DNA templates can be PCR™ products or plasmids, as long as a promoter that is recognized by the RNA polymerase is present upstream of the region to be transcribed. Promoters for the RNA polymerases of T7, T3, and SP6 are specific sequences approximately twenty nucleotides in length that guide the initiation of RNA polymerization. To produce run-off transcripts of defined length using plasmid DNA, the template should be linearized by complete restriction enzyme digestion at a site that is separated from the promoter by the insert to be transcribed. The linearized template should be stored at a concentration of 0.5–1 μg/μl.
   B. Assembly of the Transcription Reaction
   Thaw the transcription reagents (shown in the table below) and place them on ice. Then vortex the 10X Transcription Buffer (200 mM NaCl, 400 mM Tris (pH 8.0), 60 mM MgCl$_2$, 20 mM Spermidine HCl, 100 mM DTT) and ribonucleotide solutions until no precipitate is visible. Add the following amounts of the indicated reagents in the order shown to a microfuge tube at room temperature:

| | Radio-isotopically labeled probes* | Non-isotopically labeled probes** |
|---|---|---|
| Nuclease-free dH$_2$O | to 20 μl final volume | to 20 μl final volume |
| DNA template | 0.1–0.5 μg | 0.1–0.5 μg |
| 10X Transcription Buffer | 2 μl | 2 μl |
| 10 mM ATP | 1 μl | 1 μl |
| 2 mM C(α thiol)TP | 1 μl | 1 μl |
| 10 mM GTP | 1 μl | 1 μl |
| 10 mM UTP | 0–1 μl | 0–1 μl |
| Labeled UTP | 1–5 μl | 0.1–2 μl |
| SP6, T3, or T7 RNA polymerase + ribonuclease inhibitor | 2 μl | 2 μl |

*Usually $^{32}$P-labeled UTP is used. [α-$^{32}$P]-CTP cannot be used for labeling, as the modified CTP included in the kit is required for probe degradation and removal). The inventors recommend using 3 μM final concentration of limiting nucleotide for transcripts up to 400 nucleotides in length. For synthesis of RNA transcripts longer than 400 nucleotides, a higher concentration of limiting nucleotide may be needed. The unlabeled UTP in the kit is provided for this purpose. To ensure maximum specific activity, a dilution series of unlabeled UTP should be used to identify the lowest concentration of UTP required to provide adequate full-length product.
**Nonisotopic labeling should not be done with an analog of CTP, as the modified CTP provided in the kit is required for the specific degradation of the probe. If labeling with an analog of GTP or ATP, add 1 μl 10 mM UTP and decrease the unlabeled counterpart of the labeled nucleotide being used to achieve a final concentration of 0.5 mM.
[Note: Precipitation of spermidine in the 10X Transcription Buffer can lead to precipitation of the template DNA if the reaction is assembled on ice.]

Mix the reaction contents by flicking with finger or pipetting, and then microfuge tube briefly to collect all of the reaction mixture at the bottom of the tube.
   C. Incubation of Reaction
   Incubate reactions for 1 hour at 22° C.–37° C. The reactions will reach 80–90% completion after one hour and can be left for 2 hours to maximize yield. The exact incubation temperature is not critical. Little difference in yield has been seen between incubation at room temperature or at 37° C. with the actin control template.
   D. Termination of the Reaction and Recovery of RNA Probe
   Although the transcription reaction can be added directly to a hybridization reaction, storage of part or all of the reaction should be preceded by addition of 1 μl of 0.5 M EDTA to the 20 μl reaction.
II. Production of the Northern Blot
   A. Preparation of Gel
   For every 100 ml of agarose gel needed, use 1 gram of agarose and 90 ml of DEPC-treated water. Melt the agarose in a microwave or on a hotplate, cool to 50–60° C. and, in a well ventilated area or underneath a hood, add 10 ml 10×Denaturing Gel Buffer (400 mM MOPS, 100 mM sodium acetate (pH 7), 20 mM EDTA, 50% formaldehyde) and mix well. Pour the gel to about 0.6 cm in thickness. After the gel has set, it is no longer necessary to keep it under a ventilating hood. Dilute the 10× Gel Running Buffer (400 mM MOPS, 100 mM sodium acetate (pH 7), 20 mM EDTA, ) to 1× with DEPC-treated water and cover the gel to a depth of about 0.5 to 1 cm. The buffer should be circulated if the gel run will exceed three hours.
   B. Preparation and Electrophoresis of Sample RNA
   The sample RNA (up to 20 μg total RNA or poly (A+) RNA) and size markers (if used) should be suspended in DEPC-treated water in a volume not to exceed ¼ of the capacity of the wells. Add three volumes of the Northern Sample Loading Dye to the sample RNA. Incubate the samples for 15 minutes at 65° C., briefly spin the samples down, and place on ice. Optionally, ethidium bromide may be added to the samples to a final concentration of 10–50 µg/ml. However, there is a loss of sensitivity with EtBr staining (See Section III B herein below). Load the RNA on the gel, using RNase-free pipette tips, and run the gel at 5 V/cm, as measured between the electrodes.

C. Capillary Transfer to the Membrane

If ethidium bromide has been added to the samples, the gel may be photographed with UV light on a transilluminator prior to transfer. If the samples were not stained, the lane containing the size markers should be cut off and stained separately (in 1× Gel Running Buffer with 0.5 µg/ml ethidium bromide added; the buffer remaining in the electrophoresis chamber can be used for this purpose.) and photographed as above.

Assemble a downward transfer apparatus (Chomczynski, 1992). Use transfer buffer (750 mM NaCl, 75 mM Trisodium Citrate, 10 mM NaOH) in the buffer reservoir. Allow the transfer to continue for ten minutes per millimeter of gel thickness (one hour for a 6 mm thick gel) not to exceed 2 hours. The transfer can be verified by noting the movement of the blue dyes from the gel to the membrane. Disassemble the transfer apparatus, remove the membrane with forceps, and briefly (ten seconds) rinse in 1× Gel Running Buffer to remove salt and agarose. The buffer remaining in the electrophoresis chamber can be used for this purpose.

The RNA should be crosslinked to the membrane immediately after transfer and rinsing, for example by UV illumination. Crosslinked membranes can be stored at −20° C. in a vessel that will protect them from mechanical damage (i.e., rolled up in a 50 ml conical tube).

III. Probing the Northern Blot

Prehybridize the membrane in 10 ml preheated Prehybridization/Hybridization Solution (50% formamide, 375 mM NaCl, 37.5 mM Trisodium Citrate, 7% SDS) per 100 $cm^2$ of membrane at the same temperature as the expected hybridization temperature. In general, this will be 65° C. for RNA probes and 42° C. for DNA probes. The duration of prehybridization should be at least 30 minutes, but longer incubation is acceptable.

Prepare the hybridization solution by adding 1–5×$10^6$ cpm per ml of radiolabeled probes or 0.1 nM of nonisotopically labeled probe to 10 ml Prehybridization/Hybridization Solution. Remove all of the liquid from the prehybridization and quickly replace it with the hybridization solution containing the probe. Hybridization is incubated at the desired temperature, for example 55° C., overnight (8–16 h). After the incubation, pour out the hybridization solution into an appropriate container for disposal.

IV. Washing and Detection

Add 20 ml per 100 $cm^2$ membrane of Wash Solution #1 (300 mM NaCl, 30 mM Trisodium Citrate, 0.1% SDS) at room temperature to the bag or tube. Agitate for at least 5 minutes, remove and discard the solution, then repeat. When using radiolabeled probes, these washes will be radioactive and should be discarded appropriately.

Preheat 40 ml per 100 $cm^2$ membrane of Wash Solution #2 (15 mM NaCl, 1.5 mM Trisodium Citrate, 0.1% SDS) to the final, stringent wash temperature. Using 20 ml of the preheated Wash Solution #2, wash for 15 minutes at the final, stringent wash temperature with agitation. Discard this solution, add the remaining 20 ml, and repeat.

If a radiolabeled probe was used, remove the blots from the final wash and wrap them in plastic wrap or report covers to prevent them from drying out during or after autoradiography. Do not allow the blot to dry out at any time or it will become difficult or impossible to remove the probe for subsequent analysis. If a nonisotopic probe has been used, follow the manufacturer's recommendations for detection.

V. Removing the Hybridized RNA Probe from the Blot

After probe hybridization, the blots should not be allowed to dry as this makes it very difficult to remove the probe. Following detection of a hybridized probe, place the blot or blots in a bottle or tube. Dilute 20% SDS 200-fold to provide a 0.1% solution. Enough 0.1% SDS should be made to accommodate three washes (degradation, reconstitution, and wash). 10 ml/wash is sufficient to treat a membrane of 100 $cm^2$.

Dilute the 500× Probe Degradation Buffer (500 mM $I_2$ dissolved in 100% EtOH) to 1× in 0.1% SDS. Make up 10 ml/100 $cm^2$ of membrane. Add 1× buffer to the bottle or tube containing the blot. Incubate for ten minutes at 55–68° C., then discard the solution. The blot should be pale orange at this point in the protocol.

Dilute the 200× Blot Reconstitution Buffer (1 M sodium thiosulfate) to 1× in 0.1% SDS. Make up 10 ml/$cm^2$ of membrane. Add 1× buffer to the bottle or tube containing the blot. Incubate for ten minutes at 55–68° C., then discard the solution. The blot should be white, with no hint of orange remaining. Add the remaining 0.1% SDS to the bottle or tube containing the blot and incubate for ten minutes at 55–68° C. Remove the solution and store the blot for future use.

A temperature range is provided for the washes. The temperature that is used should be based on convenience, i.e., if a hybridization oven is normally set at 55° C. then use that oven for stripping the probe. The efficiency of probe removal is sequence dependent, thus higher wash temperatures (68° C., for instance) might be required to completely remove some probes.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,137,814
U.S. Pat. No. 5,380,833
U.S. Pat. No. 5,430,136
U.S. Pat. No. 5,536,649
U.S. Pat. No. 5,552,538
U.S. Pat. No. 5,578,717
U.S. Pat. No. 5,629,150
Alwine, Kemp, Stark, "Methods for Detection of Specific RNAs in Agarose Gels by Transfer to diazobenzyloxymethyl-paper and hybridization with DNA probes," *Proc. Natl. Acad. Sci., USA*, 74:5350, 1977.

Ausubel, F.M. et al., "Current Protocols in Molecular Biology," John Wiley & Sons, New York, 1989.

Brody, "Nucleotide positions responsible for the processivity of the reaction of Exonuclease I with oligodeoxynucleotide," *Biochemistry*, 30:7072–80, 1991.

Brown, Tlsty, Schimke, "Enhancement of Methotrexate resistance and Dihydrofolate reductase Gene Amplification by Treatment of Mouse 3T6 Cells with Hydroxyurea," *Mol. Cell. Biol.*, 3:1097, 1983.

Caruthers, Barone, Beaucage, Dodds, Fisher, McBride, Matteucci, Stabinsky, Tang, "Chemical synthesis of deoxyoligonucleotides by the phosphoramidite method," *Methods Enzymol.*, 154:287–313, 1987.

Chee, Yang, Hubbell, Berno, Huang, Stern, Winkler, Lockhart, Morris, Fodor, "Accessing Genetic Information with High-Density DNA Arrays," *Science*, 274:610–614, 1996.

Chomczynski, "Solubilization in Formamide Protects RNA from Degradation," *Nucl. Acids Res.*, 20:3791, 1992.

Feinberg and Vogelstein, "A technique for radiolabeling DNA restriction endonuclease fragments to high specific activity," *Anal. Biochem.*, 132:6, 1983.

Fodor, Read, Pirrung, Stryer, Lu, Solas, "Light-directed, spatially addressable parallel chemical synthesis," *Science*, 251:767–773, 1991.

Frasier, Walker, Schram, "Decontamination of Nucleic Acid Amplification Reactions Using UDG," U.S. Pat. No. 5,536,649, 1996.

Gish and Eckstein, "DNA and RNA Sequence Determination Based on Phosphorothioate Chemistry," *Science*, 240, 1520–22, 1988.

Green, Maniatis, Melton, "Human β-globin pre-mRNA synthesis in vitro is accurately spliced in Xenopus oocyte nuclei," *Cell*, 32:681, 1983.

Grunstein and Hogness, "Colony Hybridization: A Method for the Isolation of Cloned DNAs that Contain a Specific Gene," *Proc. Natl. Acad. Sci., USA*, 72:3961, 1975.

Hofler, DeLellis, Wolfe, "In situ Hybridization and Immunohistochemistry," *Adv. Immunohistochemistry*, pp 47–66, 1988.

Hough and Bass, "Purification of the Xenopus laevis Double-stranded RNA Adenosine Deaminase," *J. Biol. Chem.*, 269:9933–39, 1994.

Huang, Stump, Weiss, Caldwell, "Binding of biotinylated DNA to streptavidin-coated polystyrene latex: Effects of chain length and particle size," *Anal. Biochem.*, 237:115–122, 1996.

Kafatos, Jones, Efstratiadis, "Determination of Nucleic Acid Sequence Homologies and Relative Concentrations by a Dot Hybridization Procedure," *Nucl. Acids Res.*, 7:1541, 1979.

Kelly, Cozzarelli, Deutscher, Lehman, Kornberg, "Enzymatic synthesis of deoxyribonucleic acid. XXXII. Replication of duplex deoxyribonucleic acid by polymerase at a single strand break," *J. Biol. Chem.*, 245:39, 1970.

Kwoh, Davis, Whitfield, Chappelle, DiMichele, Gingeras, "Transcription-Based amplification system and detection of amplified human immunodeficiency virus type 1 with a bead-based sandwich hybridization format," *Proc. Natl. Acad. Sci. USA*, 86:1173–77, 1989.

Longo, Berninger, Hartley, "Use of uracil DNA glycosylase to control carry-over contamination in polymerase chain reactions," *Gene*, 93:125–128, 1990.

Mag, Luking, Engels, "Synthesis and Selective Cleavage of an Oligodeoxynucleotide Containing a Bridged Internucleotide 5'-Phosphorothioate Linkage," *Nucl. Acids Res.*, 19:1437–41, 1991.

Maniatis, Fritsch, Sambrook, Molecular Cloning, A Laboratory Manual, Cold Spring Harbor Laboratory Press, 1989.

Maniatis, Fritsch, Sambrook, Molecular Cloning, A Laboratory Manual, Cold Spring Harbor Laboratory Press, 1982.

Nakamaye, Gish, Eckstein, Vosberg, "Direct Sequencing of Polymerase Chain Reaction Amplified DNA Fragments Through the Incorporation of Deoxynucleotide α-thiotriphosphates," *Nucl. Acids Res.*, 16:9947–59, 1988.

Rashtchian and Berninger, "Use of Exo-Sample Nucleotides in Gene Cloning," U.S. Pat. No. 5,137,814, 1992.

Scadden and Smith, "A Ribonuclease Specific for Inosine-Containing RNA: A Potential Role in Antiviral Defence," *EMBO Journal*, 16:2140–2149, 1997.

Schatz, Leberman, Eckstein, "Interaction of Escherichia coli tRNA$^{ser}$ with its Cognate Aminoacyl-tRNA Synthetase as Determined by Footprinting with Phosphorothioate-Containing tRNA Transcripts," *Proc. Natl. Acad. Sci. USA*, 88:6132–6, 1991.

Southern, "Detection of Specific Sequences among DNA Fragments Separated by Gel Electrophoresis," *J. Mol. Biol.*, 98:503, 1975.

Tabor and Richardson, "A bacteriophage T7 RNA polymerase/promoter system for controlled exclusive expression of specific genes," *Proc. Natl. Acad. Sci., USA*, 82:1074, 1985.

Urdea and Horn, "Nucleotides for Introducing Selectably Cleavable and/or Abasic Sites Into Oligonucleotides," U.S. Pat. No. 5,578,717, 1996a.

Urdea and Horn, "Oligonucleotides Containing Selectably Cleavable and/or Abasic Sites," U.S. Pat. No. 5,430,136, 1995.

Urdea and Horn, "Oligonucleotides with Cleavable Sites," U.S. Pat. No. 5,552,538, 1996b.

Urdea, "Polynucleotide Reagents Containing Selectable Cleavage Sites," U.S. Pat. No. 5,380,833, 1995.

Woolford and Dale, "Simplified Procedures for Detection of Amplified DNA Using Fluorescent Label Incorporation and Reverse Probing," *FEMS Microbiol Lett*, 78:311–16, 1992.

Wyrzykiewicz, "Methods for Characterizing Phosphorothioate Oligonucleotides," U.S. Pat. No. 5,629,150, 1997.

What is claimed is:

1. A method of stripping a nucleic acid probe from a sample nucleic acid, said sample nucleic acid attached to a solid support, comprising:

a) obtaining a solid support with a sample nucleic acid attached thereto;

b) obtaining a nucleic acid probe, said nucleic acid probe comprising at least a first phosphorothioate bond;

c) admixing said nucleic acid probe with said solid support to allow association of said nucleic acid probe with said sample nucleic acid;

d) cleaving said phosphorothioate bond of said nucleic acid probe with iodine;
e) removing said nucleic acid probe from said sample nucleic acid; and
f) admixing sodium thiosulfate with said solid support, thereby removing excess iodine from said solid support.

2. The method of claim 1, wherein said nucleic acid probe comprises DNA.

3. The method of claim 1, wherein said nucleic acid probe comprises RNA.

4. The method of claim 1, wherein said nucleic acid probe comprises at least a first uracil residue.

5. The method of claim 1, wherein the concentration of said iodine is between about 0.1 mM and about 25 mM.

6. The method of claim 1, wherein said sample nucleic acid comprises DNA.

7. The method of claim 1, wherein said sample nucleic acid comprises RNA.

8. The method of claim 1, wherein said solid support is a membrane.

9. The method of claim 8, wherein said membrane is a nitrocellulose membrane or a nylon membrane.

10. The method of claim 1, wherein said solid support is a resin.

11. The method of claim 10, wherein said resin is an ion exchange chromatography resin or an affinity chromatography resin.

12. The method of claim 1, wherein said solid support is plastic.

13. The method of claim 1, wherein said solid support is a magnetic bead.

14. The method of claim 1, wherein said solid support is glass.

15. The method of claim 1, wherein said solid support is a microchip.

16. The method of claim 1, comprising separating said sample nucleic acid by electrophoresis prior to attachment to said solid support.

17. The method of claim 1, comprising cleaving said sample nucleic acid by an enzyme prior to separation by electrophoresis.

18. A kit for removing a nucleic acid probe from a sample nucleic acid, comprising, in a suitable container:
a) probe degradation buffer comprising iodine;
b) reconstitution buffer comprising sodium thiosulfate;
c) nucleotides;
d) a nucleic acid polymerase;
e) RNase inhibitor; and
f) transcription buffer.

* * * * *

UNITED STATES PATENT AND TRADEMARK OFFICE
CERTIFICATE OF CORRECTION

PATENT NO. : 6,365,731 B1
DATED : April 2, 2002
INVENTOR(S) : Brown et al.

It is certified that error appears in the above-identified patent and that said Letters Patent is hereby corrected as shown below:

<u>Column 24,</u>
Line 14, please delete "claim 1" and insert -- claim 16 -- therefor.

Signed and Sealed this

Twenty-second Day of October, 2002

Attest:

Attesting Officer

JAMES E. ROGAN
Director of the United States Patent and Trademark Office